United States Patent
Pfeiffer et al.

[11] Patent Number: 5,902,253
[45] Date of Patent: May 11, 1999

[54] APPARATUS FOR ANALYZING BODY FLUIDS

[75] Inventors: Georg Pfeiffer, Djursholm; Pontus Von Bahr, Stockholm, both of Sweden

[73] Assignee: Siemens-Elema AB, Solna, Sweden

[21] Appl. No.: 08/873,109

[22] Filed: Jun. 11, 1997

[30] Foreign Application Priority Data

Jun. 11, 1996 [SE] Sweden ................................ 9602298

[51] Int. Cl.⁶ ............................................... A61B 5/00
[52] U.S. Cl. ........................ 600/584; 600/573; 600/575
[58] Field of Search ................................ 600/573, 575, 600/578, 584, 581, 582

[56] References Cited

U.S. PATENT DOCUMENTS

| | | | |
|---|---|---|---|
| 4,077,395 | 3/1978 | Woolner | 600/575 |
| 4,535,786 | 8/1985 | Kater | 604/4 |
| 4,696,309 | 9/1987 | Stephan | 600/575 |
| 5,035,704 | 7/1991 | Lambert et al. | 600/584 |
| 5,037,396 | 8/1991 | Streeter | 604/152 |
| 5,165,406 | 11/1992 | Wong | 600/573 |
| 5,225,063 | 7/1993 | Gumbrecht et al. | 204/402 |
| 5,325,853 | 7/1994 | Morris et al. | 600/573 |
| 5,325,867 | 7/1994 | Skrabal et al. | 600/578 |
| 5,505,828 | 4/1996 | Wong et al. | 600/573 |
| 5,638,828 | 6/1997 | Lauks et al. | 600/573 |

FOREIGN PATENT DOCUMENTS

| | | |
|---|---|---|
| 2 165 216 | 10/1985 | United Kingdom . |
| WO 94/10558 | 5/1994 | WIPO . |

*Primary Examiner*—Max Hindenburg
*Assistant Examiner*—Charles Marmor, II
*Attorney, Agent, or Firm*—Hill & Simpson

[57] ABSTRACT

An arrangement for analyzing body fluids drawn from a living subject has a fluid sample station connectable to the subject for drawing fluid from the subject, a disposable cassette connectable to the fluid sample station for receiving a fluid sample to be analyzed, a sensor unit for analyzing the fluid sample, a cassette store in which a plurality of disposable cassettes are storable and a transfer system for bringing cassettes in the cassette store, one by one, into operative connection with the fluid sample station. A control unit controls the transfer system to bring the respective cassettes into connection with the fluid sample station at a programmable rate.

21 Claims, 5 Drawing Sheets

APPARATUS FOR ANALYZING BODY FLUIDS

BACKGROUND OF THE INVENTION

1. Field of the Invention

The present invention relates to an apparatus for analyzing body fluids drawn from a living subject of the type having a fluid sample station connectable to the subject for drawing therefrom, a disposable cassette connectable to the fluid sample station for receiving a fluid sample to be analyzed, at least one sensor unit for analyzing the fluid sample and a control unit.

2. Description of the Prior Art

During intensive care, for example, it is important to collect information of the condition of the patient on a regular basis in order to provide an optimal treatment for the patient. Important information can be obtained by analyzing body fluids drawn from the patient, especially blood. A blood sample can be analyzed as to its blood gas content, e.g. partial pressure of oxygen ($PaO_2$). Other parameters of interest in body fluids are pH, glucose, partial pressure of carbon dioxide ($PaCO_2$), etc.

Historically, hospitals have made use of large central laboratories for analyzing samples taken from the patients, including blood samples. Although the laboratories can provide good measurements by using complex and expensive equipment, this system has some vital drawbacks when analysis of blood gas content is considered. The blood samples taken from the patient are not analyzed immediately and the result of the analysis can, therefore, not normally be reliably used for determining necessary and/or immediate changes in the treatment of the patient. The physician sometimes, particularly in acute cases, cannot await the result of an analysis of a sample which has to be transported to a laboratory.

In addition, such a conventional laboratory does not allow for the treatment Of patients with so called closed loop-systems (i.e. infusion, medication, ventilation, anaesthesia systems), for which the continuous or semi-continuous sample and analysis of body fluids is mandatory in order to acquire the necessary parameters for regulating the whole system.

Further, for parameters such as the blood gas content of blood, there is also the necessity of keeping the blood sample from contact with air which otherwise could affect the blood gas content in the blood sample.

As one approach to solving these problems, smaller mobile systems have been developed, i. e., point of care systems (for analyzing blood gas content). The point of care systems can be brought to the patient's bedside and usually include a measurement unit and a disposable cassette containing the sensors. A physician or nurse draws a blood sample from a patient into a cassette and analyzes it by means of the point of care system.

Although operating more flexibly and faster than the use of central laboratories, the point of care systems are ineffective in providing continuous or almost continuous information about the body fluid parameter, e.g the blood gas situation of the patient. In cases where treatment is given to the patient, using technical systems or equipment, the actual settings of the system or equipment could and should be made dependent upon the continuous information of the body fluid parameter, such as the blood gas content, and therefore require more regular samples to be taken and analyzed. "Continuous" body fluid measurements are a necessity if closed loop ventilator, infusion, anaesthesia, etc. treatment is to be given, e. g. automatic control of a lung ventilator based on measured blood gas content.

Systems for (practically) continuous measurement of blood gases are known. For instance U.S. Pat. No. 5,225,063 discloses an apparatus for measuring the partial pressure of oxygen, wherein a double lumen catheter is inserted into the patient's blood system. The outer lumen extends further into the blood system than the inner lumen, thereby almost enclosing the inner lumen. Blood can be drawn into the inner lumen, by a first pump, up to a measuring cell where a measurement is made. After measurement a second pump will pump a rinse medium through the outer lumen toward the blood system and the rinse medium will be pumped into the inner lumen to cleanse the lumen and the measuring cell from all blood residues before next blood sample is taken.

Another system of a similar kind is described in U.S. Pat. No. 4,535,786. In this system the blood sample is drawn to a measuring cell and is returned to the patient together with rinse medium after measurement.

These (almost) continuous measurement systems have some disadvantages. The sensors used in the measuring cell must be stable over a long time and usually require regular calibration as well. Such systems normally also require a very exact pumping system for drawing the blood sample, rinse medium and calibration solution in exact volumes. This requires exact (and expensive) pumps or advanced measurement systems for measuring the pumped volumes. Further, when frequent samples are taken, the successive minimum volumes required by the pump system additively result in an unacceptable loss of blood. Depending on the system design, some systems will lead to a loss of blood while rinse medium and calibration solution will enter the blood system. In addition, these systems also carry an inherent risk for the patient, since both the rinse medium and the calibration solution must always be completely harmless substances. In general, these systems have the inherent disadvantage of being "open" in the sense that these systems "communicate" body fluids from and to the body arid from and to the system and can therefore be a potential source of infection and/or necessitate the use of relatively complex and expensive elements, procedures (e.g. sterilization) and features in order to prevent these risks.

SUMMARY OF THE INVENTION

An object of the present invention is to provide an arrangement for analyzing body fluids drawn from a living subject which overcomes the above-described disadvantages of known systems.

This object is achieved in accordance with the present invention in an analyzer arrangement of the type generally described initially above, but additionally having a cassette store, in which a number of disposable cassettes are storable, and a transfer system for bringing cassettes in the cassette store, one by one, into operative connection with the fluid sample station, and wherein the control unit controls the transfer system to bring the cassettes into connection with the fluid sample station at a programmable rate.

An arrangement thus is obtained in which disposable cassettes are taken, one at a time, by the transfer system and are individually connected to the fluid sample station where a body fluid sample is taken for analysis. After use the cassette can be brought back to the cassette store or disposed of in another appropriate manner. If used cassettes are brought back to the cassette store, it is preferable to have the entire cassette store be an interchangeable unit of the arrangement. The automatic exchange of disposable cassettes at the fluid sample station provides an arrangement which can be programmed to measure, inter alia, blood gas content at a rate which is sufficient to provide for an optimal treatment of the patient using closed loop treatment systems.

It should be noted that a change in the treatment (by a ventilator or other equipment) will normally not have an instant effect on the measured body fluid parameter (such as blood gas content) since a systemic exchange between the treatment and the body (such as the gas exchange between gases in the lungs and in the blood system) first must occur before the parameter is affected. This could in some circumstances take up to a couple of minutes, depending on the individual case and the parameter measured. It is therefore sufficient to automatically draw a body fluid sample and analyze this at a related rate.

The above object also is achieved in accordance with the invention in a further embodiment having a number of disposable sensor elements stored in a sensor element store and having a transfer system for bringing sensor elements from the store into operative connection with the cassette, the control unit controlling the transfer system to bring the sensor elements into connection with the fluid sample station at a programmable rate.

The only difference between this embodiment and the initially-described embodiment is that in this case only the sensor elements are exchanged, whereas the entire cassette is exchanged in the first case (in which the sensor elements need not be included within the disposable cassette).

DESCRIPTION OF THE PREFERRED EMBODIMENTS

Figure 1:
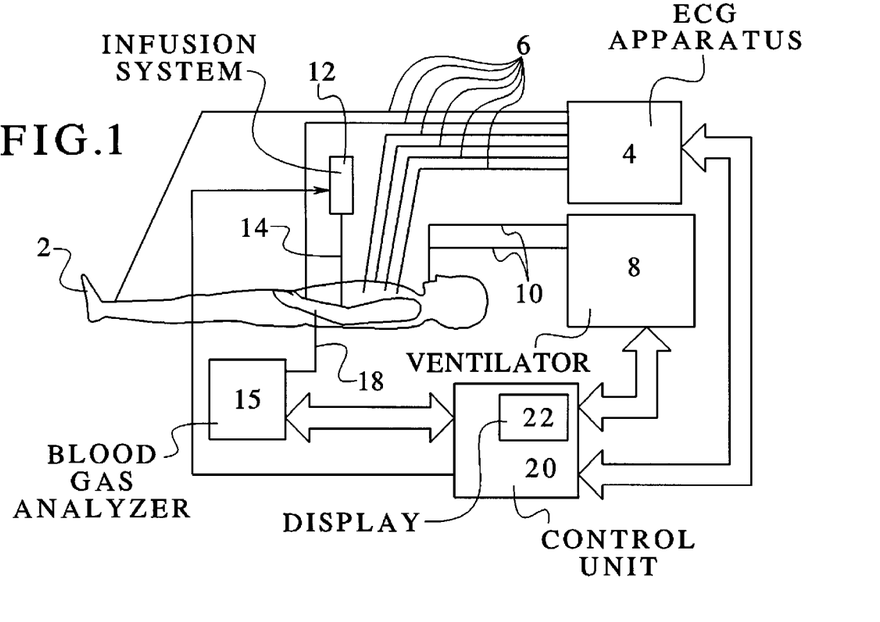
FIG. 1 shows a patient connected to intensive care equipment for treatment and monitoring.

FIG. 1 shows a patient 2 connected to a number of different medical apparatuses in an intensive care system. The patient 2 is, for instance, connected to an ECG apparatus 4 which via electrodes 6 connected at different parts on the body of the patient 2, records and analyzes the patient's heart signals. Further, a ventilator 8 is connected to the patient 2 via gas lines 10 for supporting or controlling the patient's respiration. An infusion system 12 is connected to the patient 2 via a infusion line 14 for providing the patient 2 with nutrient solution, plasma or other substances which can be infused during intensive care. An arrangement according to the invention (in this case a blood gas analyzer 16) is connected to the patient 2 via a catheter 18 for drawing blood from the patient 2. For clarity, the catheter 18 is shown with disproportionate length. In reality, the catheter 18 should be as short as possible, particularly when blood samples are to be taken. The arrangement 16 will therefore normally be located very close to, if not in direct contact with, the patient 2.

A central control unit 20 is connected to all of the apparatuses 4, 8, 12 and 16 involved in the intensive care treatment and monitoring for recording, analyzing and even control or suggesting changes in the treatment given to the patient 2. A display 22 can display different curves or measurement results relating to the patient 2, such as ECGS, respiration curves, blood gas content, etc.

The arrangement 16 could also be used together with one of the other apparatuses, such as the infusion system 12 or the ventilator 8. The arrangement 16 could also be used with other apparatus, such as anaesthetic systems, dialysis machines, insulin systems, etc.

Figure 2:
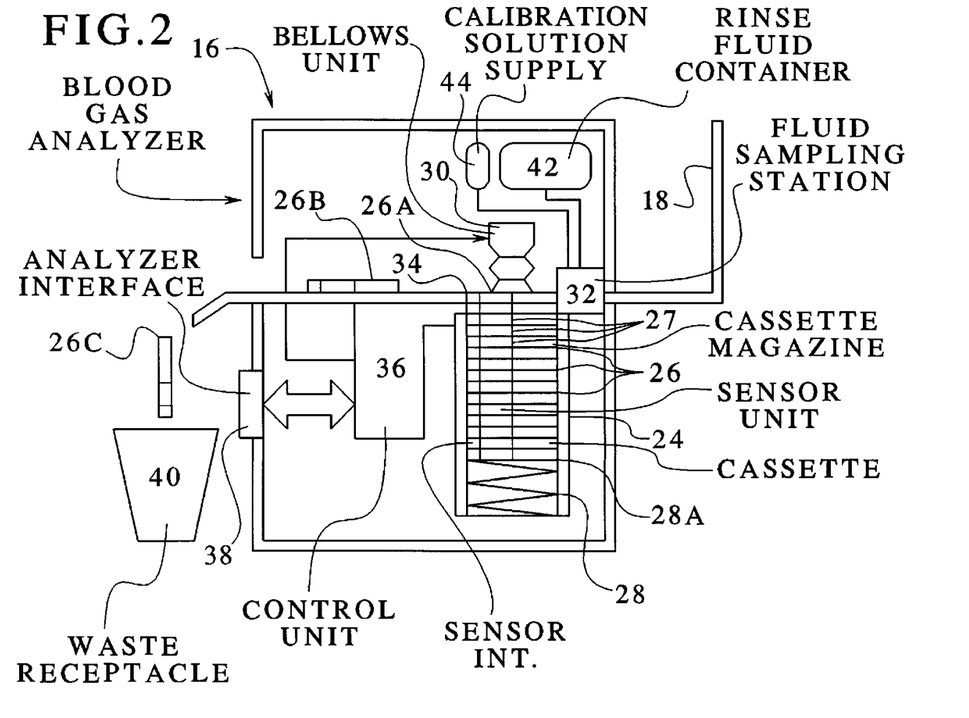
FIG. 2 shows a first embodiment of an analysis arrangement according to the invention.

A first embodiment of the arrangement according to the invention is shown in FIG. 2 as a blood gas analyzer 16. The blood gas analyzer 16 has a cassette magazine 24 for storing a stack of disposable cassettes 26. The cassette magazine 24 is controlled by a spring 28 and bellows unit 30 for feeding the cassettes 26, one by one, into operative connection with a fluid sample system 32. The fluid sample station 32 is connected to the catheter 18 for drawing blood from the patient. When the cassette magazine 24 has been emptied, it can either be replaced by another magazine loaded with a new stack of cassettes 26, or new cassettes 26 can be inserted into the empty magazine 24. In order to press down the spring 28, there is a handle 28A on the side of the magazine 24, connected to spring 28.

As shown in FIG. 2 a cassette 26A is connected to the fluid sample station 32 for receiving a blood sample to be analyzed. In this embodiment each disposable cassette 26 has a sensor unit 27 which can measure and analyze the blood sample. The sensor unit 27 can be any known optical, electrochemical or similar sensor. It is, therefore, not necessary to describe the sensor or the sensor unit 27 in further detail.

The result of the measurement is transferred via a communication interface 34 of the cassette 26A to a control unit 36. The control unit 36 also controls the transfer system composed of the spring 28 and the bellows unit 30 so that the cassettes 26 are brought into operative connection with the fluid sample station 32 at a programmed rate.

The control unit 36 can transfer information and receive instructions via an analyzer interface 38 which may then connect the blood gas analyzer 16 to the central control unit 20 shown in FIG. 1.

After a measurement has been made, the disposable cassette 26B is transported from the fluid sample station 32 to an opening of the blood gas analyzer 16 and then into a waste bag 40, as illustrated by cassette 26C.

Since the blood gas analyzis must be made on fresh blood each time, a rinse fluid container 42 is connected to the fluid sample station 32 so that a rinse fluid can be introduced into the catheter 18, thereby returning the blood within catheter 18 to the blood system of the patient. The blood consumption is thereby reduced. The rinse fluid is preferably a sodium chloride solution or other infusible solution.

A calibration solution supply 44 is also connected to the fluid sample station 32. From the calibration solution supply 44, a calibration solution can be conveyed to the connected cassette 26A for calibrating the sensor unit 27 before a blood sample is taken for analyzis. This measure is only necessary when using disposable sensor units 27 requiring calibration before use. The calibration solution will not come in contact with any medium entering the blood system and the most suitable calibration solution can therefore be used, even if it contains substances which could be harmful to the patient.

As an alternative, each cassette 26 can itself contain the calibration solution, either directly within the sensor unit 27 or in a cartridge which is opened as the cassette 26 is connected to the fluid sample station 32.

Each cassette 26 may also include a filling detector (not shown) for determining when a sufficient amount of blood has been pumped into the cassette 26. Such a filling detector could be arranged to optically detect the presence of blood in the cassette or by measuring resistance at a certain level within the cassette 26, thereby detecting that blood has filled the cassette 26 to a certain level. other detectors can also be used, in particular detectors known for use in the other described apparatuses.

Figure 3:
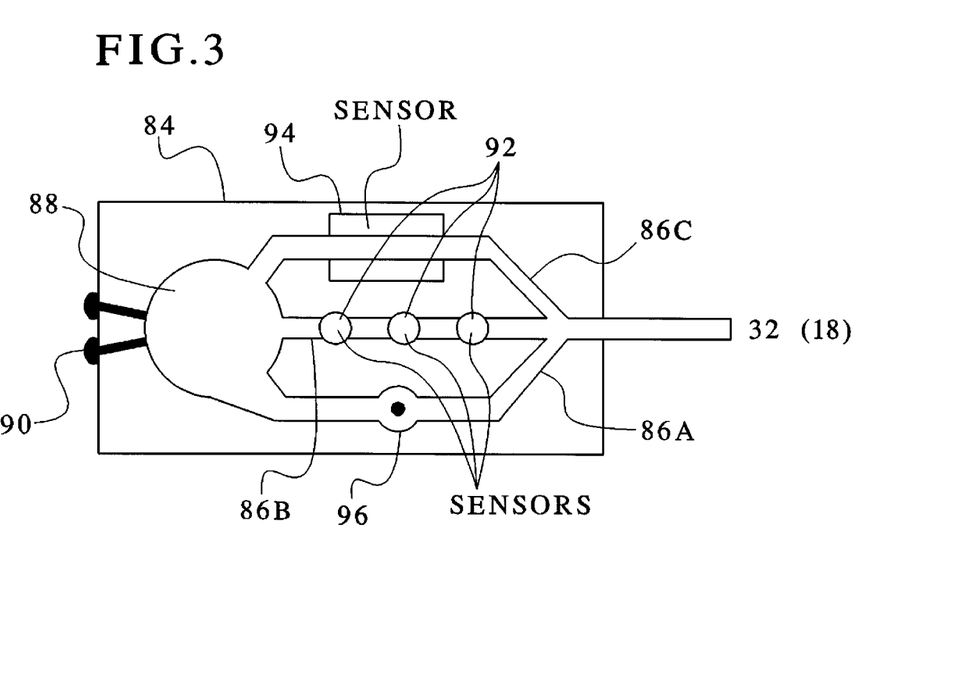
FIG. 3 shows an example of a disposable cassette used in the arrangement of FIG. 2.

One example of how the cassette can be constructed is shown in FIG. 3. A cassette housing 84 contains a capillary system 86 which is connectable at one end to the catheter 18 via the fluid sample station 32 in FIG. 2. The capillary system has a first capillary 86A, a second capillary 86B and a third capillary 86C. In the other end of the cassette housing 84 a cavity 88 is located. The cavity 88 is connectable to a suction/pump system (not shown) via a suction/pressure nipple 90 when the cassette housing 84 is brought into its operating position.

The cavity 88 is used as a reservoir for any "old" blood, rinse medium or calibration solution which may be present in the catheter 18 when the cassette housing 84 is connected to the catheter 18. When the cassette is filled with blood for new measurement, the cavity 88 will be filled with the "old" fluids via the first capillary 86A, which has a somewhat larger area or lower flow resistance. When the "old" fluids have filled the first capillary 86A and part of the cavity 88, a microvalve 96 located in the first capillary 86A closes and a new and fresh blood sample fills the second capillary 86D and the third capillary 86C. Electrochemical sensors 92 are arranged in, the second capillary 86B and an optical sensor 94 is arranged in the third capillary 86C, for analyzing the fresh blood sample.

Since fresh blood is always taken from the patient, the risk of infection or contamination is minimized.

The size of the cavity 88 and the first capillary 86A are selected to match the fluid volume which it is necessary to receive in order to remove "old" fluids and ensure that a fresh blood sample fills the second capillary 86B and the third capillary 86C so that the sensors 92 and 94 are covered with the sample. It is then not necessary to have a further waste bag system (such as 40) for removing the "old" blood, rinse medium, calibration solution etc. All is taken care of within the disposable cassette housing 84 itself.

It is also possible to use completely separate capillaries for the "old" fluids and the new sample. In such a case it is preferable to use two separate nipples 90 at the end of the cassette housing 84.

Alternatively, the filling of the capillary system 86 can be controlled by using a sensor element to ensure that a fresh sample is collected.

If the calibration solution (and/or rinse medium) is mixed so that it has a definite difference in an identifiable characteristic compared to the drawn blood, it will be quite easy for the control unit 36 to interrupt the sampling of the blood just when the sensors 92 and 94 are covered with the fresh blood sample. This minimizes the loss of blood for the patient 2, which is very important. The sensors 92 can, as mentioned, be optical, electrochemical or a combination of both.

Figure 4:
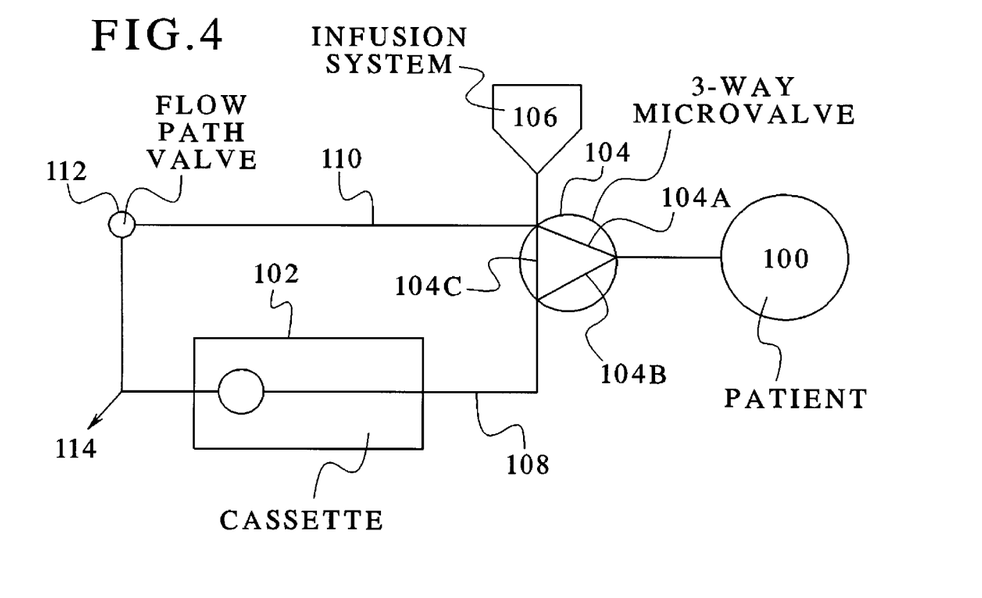
FIG. 4 shows an example of a fluid sample station of the arrangement of FIG. 2.

In FIG. 4 an example of a fluid sample station connected to a patient 100 is shown. The fluid sample station can receive a disposable cassette 102, which is connectable to the patient via a 3-way microvalve 104. The 3-way microvalve 104 can simultaneously open one or more of a first flow path 104A, a second flow path 104B and a third flow path 104C for a flow of fluids. Also connected to the 3-way microvalve 104 is an infusion system 106. The infusion system 106 has an infusion medium to be supplied to the patient 100. Ordinarily, flow path 104A is open to allow a controlled flow of infusion medium to flow to the patient 100. Using this combination, the infusion system 12 and the arrangement 16 in FIG. 1. can be integrated into a single unit or apparatus.

When a sample of a body fluid, in this case blood, is to be taken from the patient 100, the first flow path 104A is closed and the second flow path 104B is opened. By using a suction system (not shown, but connected to lumen 114) a blood sample can be drawn from the patient 100 into the cassette 102 for analyzis. The cassette 102 could be identical to the cassette housing 84 shown in FIG. 3.

When the blood sample has been taken, the second flow path 104B is closed and the first flow path 104A is opened again for supplying infusion medium to the patient. For cleansing the catheter portion 108 between the cassette 102 and the 3-way microvalve 104, the third flow path 104C could be opened for a specific period of time. Supply from the infusion system 106 should then be increased accordingly to ensure that the patient receives a sufficient amount of infusion medium. The infusion system 106 and the sampling operation should be controlled together for optimizing their functioning and in particular for compensating for the loss of infusion medium. The infusion medium may in some instances even be used for calibration of the sensor elements (not shown) in the cassette 102.

The loss of infusion medium, as well as the loss of blood, can be minimized by including a further flow path 110 from the connection between the infusion system 106 and the 3-way microvalve 104. In the further flow path 110 a second valve 112 is arranged. The normal infusion and the sampling of blood is carried out as above, but then the second valve 112 is opened while the second flow path 104B remains open. The cassette 102 will now be flushed with infusion medium via the further flow path 110 and the blood sample is forced to flow toward the patient 100 via the catheter portion 108 and the second flow path 104B. When an amount of infusion medium corresponding to the amount of drawn blood has entered the flow path system (the further flow path 110, the cassette 102, the catheter portion 108 and the second flow path 104B), the normal infusion operation is activated, i.e. only the first flow path 104A is open.

As an alternative to the above fluid sample station, the 3-way microvalve 104 could be replaced with a valve having only one flow path and being able to be rotated so that the flow path can connect any two of the three corners of the triangle (104A–C). The further flow path 110 and second valve 112 are then not necessary. At first the single flow path valve is set so that the flow path connects the infusion system 106 and the patient 100. When a sample is to be taken, then the valve is rotated so that the flow path connects the patient, 100 and the cassette 102. Body fluids can then flow (or be drawn by suction) from the patient 100 to the cassette 102. Then the valve is rotated so the flow path opens a connection between the infusion system 106 and the cassette 102 for flushing and cleaning the catheter portion 108. Finally, the valve is rotated back to its normal infusion position.

The choice of which fluid sample station to use basically depends on which body fluid to be sampled and the amount and frequency the sampling requires. Where blood is concerned, for instance, the total amount of sampled blood should be minimized. One way of minimizing the losses is of course to return some or all of the sampled blood back to the patient.

Calibration of the sensor elements in the cassette 102 can also be made before the cassette 102 is brought into operative connection with the fluid sampling station. A calibration fluid container and flushing mechanism can in such a case be integrated with the cassette station or cassette storage. Since no contact is made between the calibration system and the patient 100, such a calibration system can be closed and the same calibration solution can be reused. Only the amount which may remain within the cassette 102 after calibration is lost and must eventually be replaced in the calibration system. The amount of calibration solution initially present in the calibration system can be selected with respect to the number of cassettes 102 to be used. Calibration can be done at one or several value points using one or several different calibration solutions. Since the cassette 102 can be rinsed free of calibration solution with a suitable rinse medium, the calibration solution can be selected from any suitable kind of calibration solution since there is then no risk that the calibration solution will come into any connection with the patient.

Figure 5:
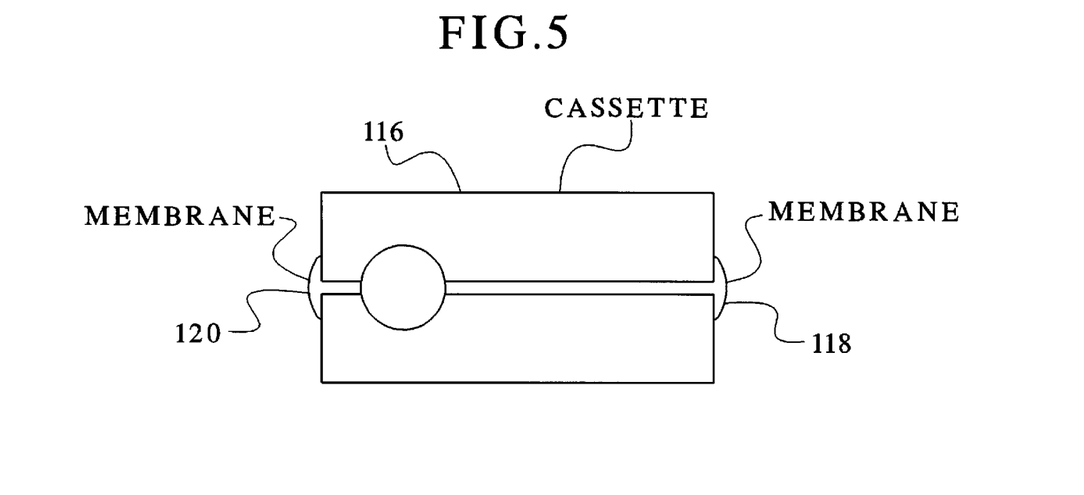
FIG. 5 shows another example of a disposable cassette used in the arrangement of FIG. 2.

As an alternative to a complete calibration solution system (integrated with or separate from the cassette station), the cassette can be filled with the calibration solution from the beginning, as shown in FIG. 5. Such a cassette 116 has a first membrane 118 in one end and a second membrane 120 in the other end. The cassette may be of any kind described above. When the cassette 116 is moved into operative connection with the fluid sample station, the membranes 118 and 120 are penetrated for removing the calibration fluid after calibration and receiving the body fluid sample for analysis.

It is of course possible to use a separate calibration station where the calibration of the sensor elements in the cassette 116 is performed and the membranes 118 and 120 are punctured for removing the calibration fluid before moving the cassette 116 to the fluid sample station. Rinsing can also be made in any of these cases.

Figure 6:
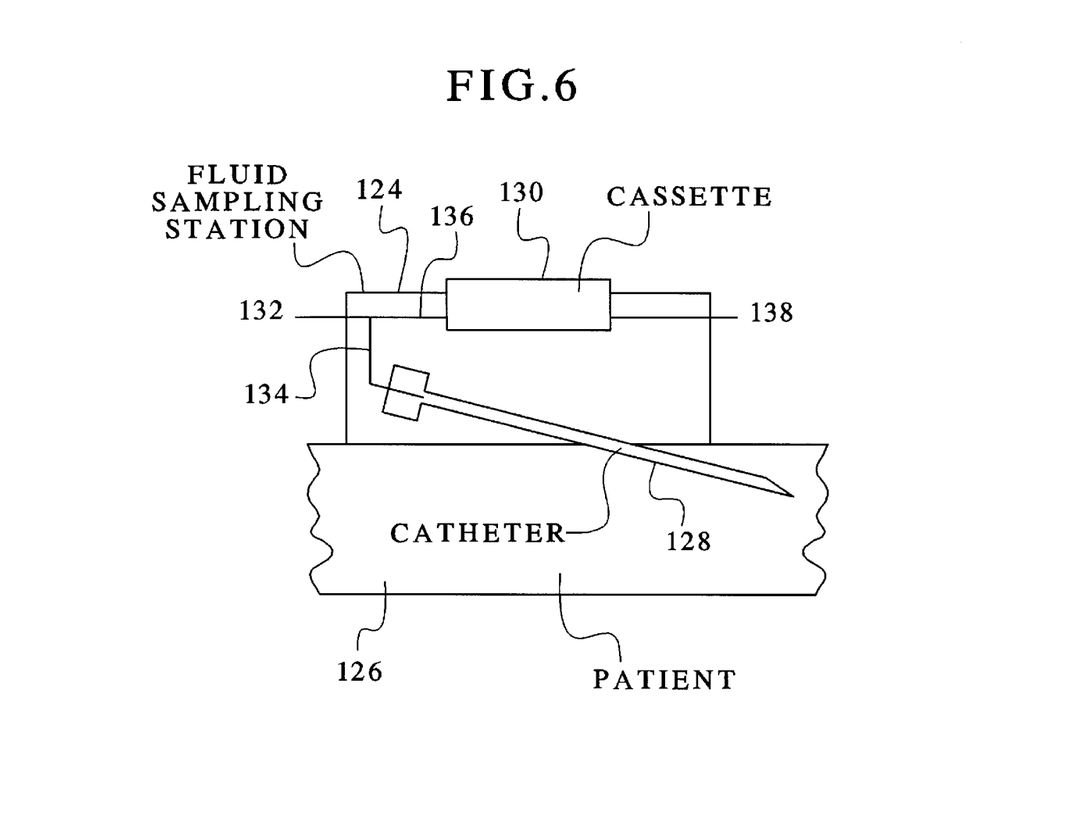
FIG. 6 shows how the arrangement of FIG. 2 can he connected to a patient.

A major advantage of the arrangement according to the invention is that the size of the arrangement can be very small, which allows for close attachment to the point of sampling on the human body. An example of this is shown in FIG. 6, where a fluid sample station 124 is in close contact with a part of a patient 126. The fluid sample station 124 has a fluid sample catheter 128 which has been inserted into the patient 126 for drawing a sample of body fluid. A cassette 130 can be inserted into the fluid sample station 124 for receiving the sample.

An infusion system (not shown) can be connected at fluid line 132 for delivering infusion fluid to the patient 126 via fluid path 134 and the catheter 128. Similarly, a calibration or rinse medium can be used instead of an infusion system (in which case a minimum amount of the medium should be allowed to enter the patient 126). At the other end of the fluid sample station 124 a connection 138 leads to a pressure or suction system for generating the required suction or pumping for drawing blood or other fluids from the body. The fluid sample station 124 can be integrated with a fixation system or mechanism for holding the fluid sample station 124 fixed against the selected part of the patient 126.

This close attachment of the fluid sample station 124 to the patient 126 allows a total length of the flow paths in the catheter 128, and flow paths 124 and 136 to the cassette 130 to be minimized to a few centimeters or even less. This results in a minimal body fluid consumption for each measurement. Such consumption is further reduced if the diameter of the lumen in the catheter 128 and the capillary system within the cassette 130 are also minimized.

Figure 7:
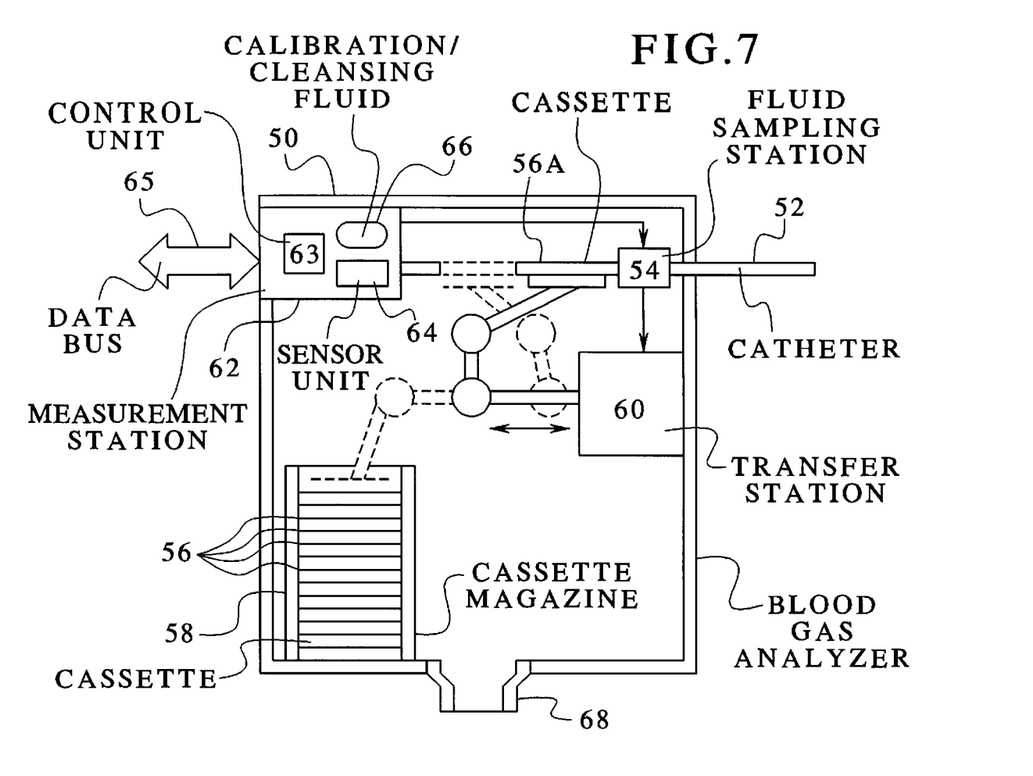
FIG. 7 shows a second embodiment of an analysis arrangement according to the invention.

In FIG. 7 a second embodiment of the arrangement is shown as a blood gas analyzer 50. The fluid sample station 54 pumps a specific amount of blood into a disposable cassette 56A. Disposable cassettes 56 are stored in a stack in a cassette magazine 58, from which they are brought to the fluid sample station 54 by a transfer system 60. The transfer system 60 is in this embodiment constructed as a (miniaturized) robot arm.

The disposable cassette 56A is thus filled with blood at the fluid sample station 54 and is then brought to a measurement station 62 by the transfer system 60. In the measurement station 62 a control unit 63 and a sensor unit 64 are located. The sensor unit 64 is brought into contact with the blood sample in the disposable cassette 56A, either by emptying the cassette 56A into a measurement cell within the sensor unit 64 or by bringing the sensor unit 64 to enter the cassette 56A. Measurements are then made and a measurement signal can be transferred via the control unit 63 and data bus 65 to a central control unit (as shown in FIG. 1).

If the blood sample has been conveyed to the sensor unit 64 it can be returned to the cassette 56A after analysis. In any case, the blood sample can either be disposed of, together with the cassette 56A, or be returned to the patient's blood system. Used cassettes 56 are disposed of via a disposal exit 68.

A calibration and/or cleansing fluid 66 is also provided for in the blood-gas analyzer 50. The sensor unit 64 can thereby be efficiently cleansed and calibrated before next blood sample is analyzed.

The advantage of using a separate measurement station 62 for the analyzis is, among other things, that cleansing fluids and calibration fluids need never come into contact with the patient's blood system. The sensor unit 64 can, therefore, be more efficiently cleansed from all blood residue after measurement has been made, since larger amounts of cleansing fluid and strong detergents can even be used for cleaning the sensor unit 64. This is particularly the case when the fluid sample station 54 is integrated with an infusion system (e. g. the infusion system in FIG. 1.). The infusion medium can then rinse all flow paths in the fluid sample station 54 before next cassette 56 is brought into operative connection with the fluid sample station 54.

The measurement station 62 includes the control unit which controls the transfer system 60 as well as the fluid sample station 54. When the cassette magazine 58 is empty, new cassettes 56 can be loaded into the magazine 58.

As an alternative, each of the cassettes 56 in this second embodiment can contain its own sensor elements and the sensor unit 64 can include the necessary equipment for reading the sensor elements (e. g. optically). If a calibration of the sensor elements is to be performed, this will be done before the cassettes 56 are filled with the blood sample. In other words, the transfer system 60 will first bring a cassette 56 from the stack 58 to the measurement station 62 for calibration of the sensor elements and then to the fluid sample station 54 for receiving the blood sample and then back again to the measurement station 62 for analysis.

In this alternative arrangement, each cassette 56 can contain a small cartridge containing the calibration solution. As the cassette SG enters the measurement station 62 for calibration, the cartridge is opened for releasing the calibration solution. It is then only necessary to have a rinse medium (cleansing fluid) in the measurement station 62.

Each cassette 56 could also be filled with the calibration solution (as described in connection with FIG. 5.).

Figure 8:
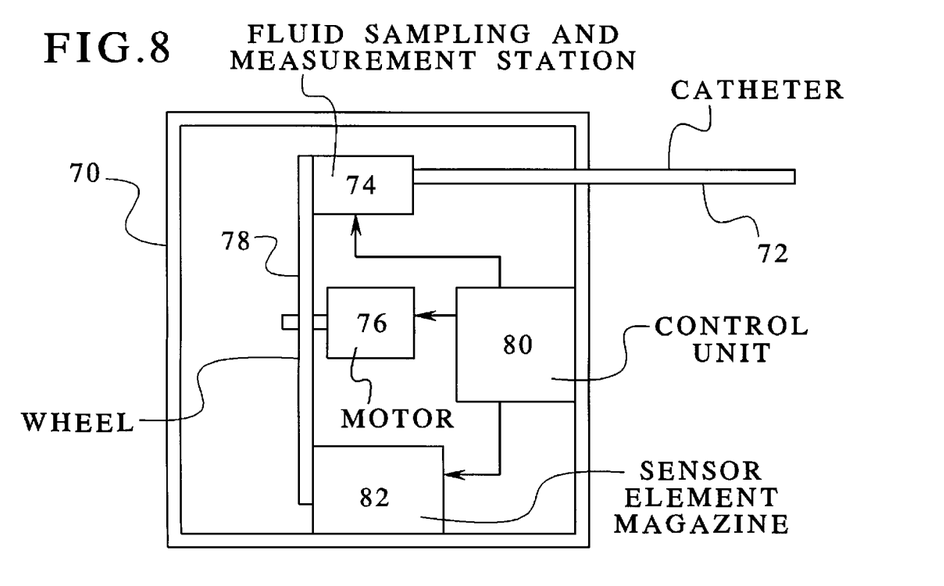
FIG. 8 shows a third embodiment of an analysis arrangement according to the invention.

A third embodiment of the arrangement according to the invention is shown in FIG. 8, wherein a blood gas analyzer 70 receives blood from a patient's blood system via a catheter 72. The blood is led into a combined fluid sample station and measurement station 74. A motor 76 drives a wheel or carrousel 78 to which sensor elements are removably applied. For each new measurement of a blood sample, a new sensor element or set of sensor elements is provided by rotating the carrousel 78 one step and connecting the new sensor element or elements to the fluid sample and measurement station 74. A sensor elements magazine 82 can be arranged for replacing used sensor elements on the carrousel 78 with new ones, thereby increasing the operation time for the blood gas analyzer 70. A control unit 80 controls the operation of the blood gas analyzer 70.

As an alternative, the sensor element(s) can be firmly attached on the carrousel 78 which itself may be exchangeable.

Figure 9:
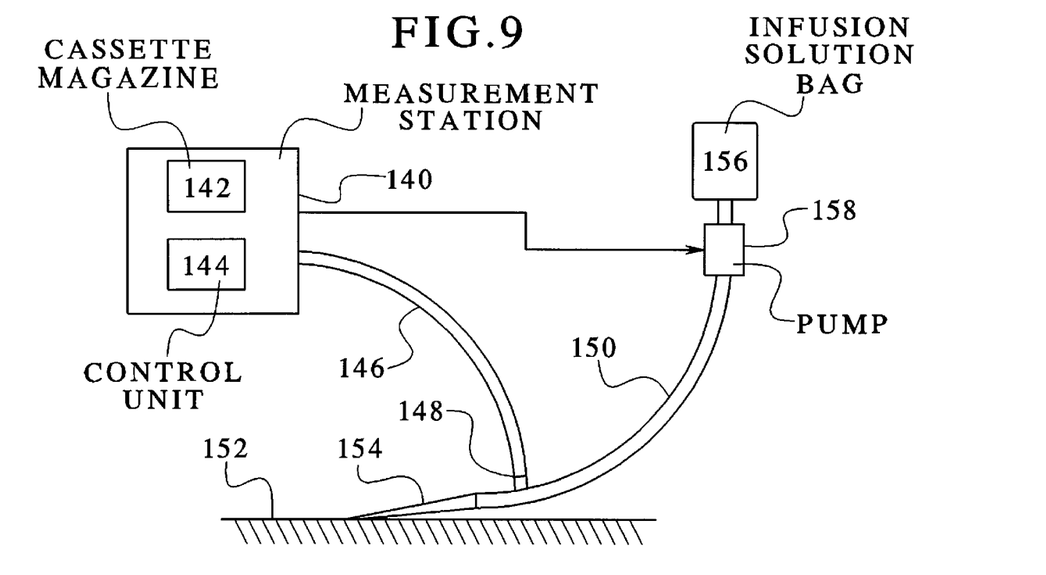
FIG. 9 shows a fourth embodiment of an analysis arrangement according to the invention.

In FIG. 9, a fourth embodiment of the arrangement is schematically shown. This embodiment of the arrangement has a measurement station 140, including a cassette store 142 and control unit 144, a transfer system 146 for disposable sample cassettes, and a fluid sample station 148, which is coupled to a catheter 150.

The catheter 150 Is at one end connected to the blood system of a patient 152 via a catheter needle 154 and at the other end to an infusion solution bag 156 and a pump 158. The pump 158 is controlled by the control unit 144 in the measurement station 140.

When a blood sample is to be taken from the patient, a disposable sample cassette is transferred from the cassette stack 142, via the transfer system 146 to the fluid sample station 148. The transfer system 146 can be a plastic tube or similar item. Transport of the disposable cassettes can be made by pneumatic, mechanical or electromagnetic transportation. By placing the stations 140 and 148 appropriately, gravity can be used for transport in one of the directions. Return of the cassette can be made by use of a string or any of the mentioned transportation means. Combinations of different transportation means are also possible.

At about the same time as a disposable cassette is transported to the fluid sample station 148, a control signal is sent to the pump 158. The pump 158 is activated to pump fluid toward the infusion solution bag 156, thereby drawing blood from the patient into catheter 150. The pump 158 is controlled to draw blood up to the fluid sample station 148.

The disposable cassette is then filled with blood (as described in more detail below) and transported back to the measurement station 140 for analysis of the blood sample.

As the disposable cassette is transported back, the pump 158 can be controlled to reverse the direction of the flow and return the blood to the patient 152 together with a sufficient amount of infusion solution for cleansing the catheter 150 of all blood residues. When combined with an infusion system, the pump 158 can be controlled to deliver infusion solution front the infusion solution bag 156 at al times (interrupted only when a blood sample is taken).

Figure 10:
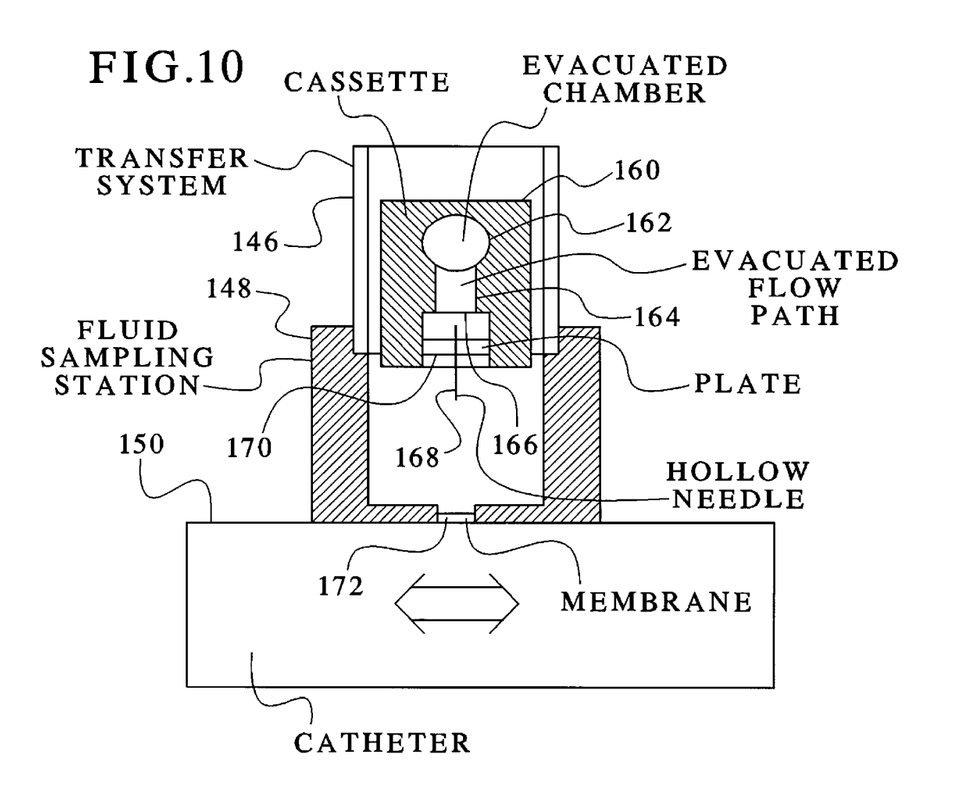
FIG. 10 shows a fluid sample station and a disposable cassette of the fourth embodiment.

One possibility of arranging the fluid sample station 148 is shown in greater detail in FIG. 10. A disposable cassette 160 is shown in the position of entering the fluid sample station 148 from the transfer system 146. The disposable cassette 160 has a cavity 162 at a negative pressure, preferably vacuum, a flow path 164 (which may include sensor means for the analysis) and a cassette membrane 166 for separating the cavity 162 and flow path 164 from the surroundings. The disposable cassette 160 further has a hollow needle 168 placed in a moveable plate 170.

The fluid sample station 148 has a sample membrane 172 which is placed in contact with the fluid in the catheter 150. When the disposable cassette 160 is forced (e. g. pneumatically) into the fluid sample station 148, the hollow needle 168 will press against the sample membrane 172. The movable plate 170 will then move backwards in the disposable cassette 160 and the hollow needle 168 will penetrate the cassette membrane 166 (which is constructed to be more easily penetrated than the sample membrane 172). Since the hollow needle 168 is pressed against the sample membrane 172, the vacuum within the disposable cassette 160 is maintained.

As the disposable cassette 160 is forced to continue its movement into the fluid sample station 148, the movable plate 170 will reach a stop (not shown) and the hollow needle 168 will penetrate the sample membrane 172, thereby opening a fluid connection between the cavity 162 and flow path 164 of the disposable cassette 160 and the fluid in catheter 150. A small amount of blood will be drawn into the disposable cassette 160 due to the vacuum within the cavity 162 and the flow path 164.

When the disposable cassette 160 is retracted from the fluid sample station 148, to be returned to the measurement station via the transfer system 146, the hollow needle 168 will first be removed from the cassette membrane 166 and then from the sample membrane 172. The sample membrane 172 and the cassette membrane 166 are both a material of the type which seals itself after removal of the hollow needle 168. Such materials are known in e. g. the technical area of implantable infusion devices (for insulin and other therapeutic drugs) and need not be further described in this case.

The disposable cassettes 160 can be made of glass or plastic. The size of the disposable cassette 160 naturally depends on the amount to be sampled. For blood analysis a sample of about 10 microliters is required. The total volume of the cavity 162 and flow path 164 should therefore be somewhat larger than 10 microliters. By using vacuum as the flow inducer, these small amounts can be taken without need of exact pumps and monitoring systems. When sampling other fluids for analysis, larger amounts may be required.

Calibration of sensors (when placed inside the disposable cassette 160) can be made after measurement of the blood.

The above embodiments only describe possible configurations of the arrangement according to the invention. In particular, it should be pointed out that the invention relates to the automation of exchanging disposable cassettes or exchanging disposable sensor elements.

Although the described embodiments mostly relate to analysis of blood gas content, the same principles are valid for analysis of all body fluids and all relevant parameters of such fluids, e.g. glucose, pH, etc.

The inventive arrangement is not restricted to the disclosed embodiments for automatically exchanging cassettes or sensor elements. For instance, a carrousel of cassettes could be used in any of the first, second and fourth embodiments and that a magazine of sensor elements could be used in the third and fourth embodiments. In principle, a person of skill in the field could select any known appropriate automation system where an object is taken from a store or similar site and is brought to another site or sites (particularly a site of operation). The field of industrial automation provides numerous examples of such systems for other purposes. Small size systems are of course preferable, in particular when small amounts of body fluids are to be taken. For some body fluids, however, (e. g. urine) relatively large volumes can be drawn and thus the size of the complete arrangement is not as important.

From the above embodiments it is also clear that the disposable cassettes could include the entirety of the equipment required for analyzing the body fluid sample, they could include sensor elements which require separate read out equipment outside the cassette and they could be used only for receiving the body fluid sample from the fluid sample station and bring this body fluid sample into contact with a sensor unit at a measurement station.

Combinations with other known systems is also possible, e. g. the system described in U.S. Pat. No. 5,225,063 could be combined with the present arrangement in such way that the measurement cell in the known system is made of disposable cassettes or equipped with exchangeable sensor elements as disclosed herein the present invention.

Although other modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for analyzing body fluids from a living subject comprising:

fluid sampling means continuously in fluid communication with to a living subject for drawing a fluid therefrom for the duration of a fluid sampling procedure;

sensor means for analyzing said fluid;

a cassette magazine containing a plurality of disposable cassettes;

transfer means for successively bringing cassettes individually from said cassette magazine into and out of fluid communication with said fluid sampling means for allowing said fluid to flow into a cassette while in fluid communication with said fluid sampling means for analysis of the fluid in the cassette by said sensor means; and control means for controlling said transfer means to successively bring said cassettes individually into and out of fluid communication with said fluid sampling means at a programmable rate.

2. An apparatus as claimed in claim 1 wherein said sensor means comprises a plurality of individual sensor units respectively contained in said plurality of disposable cassettes, and each cassette further comprising interface means for exchanging signals between the sensor unit in that cassette and said control means while that cassette is in fluid communication with said fluid sampling means.

3. An apparatus as claimed in claim 2 further comprising means for filling each cassette, while in fluid communication with said fluid sampling means, with a calibration solution for the sensor unit contained in that cassette.

4. An apparatus as claimed in claim 2 wherein each disposable cassette contains a cartridge containing calibration solution for the sensor unit contained in that cassette.

5. An apparatus as claimed in claim 2 wherein said fluid sampling means comprises a supply of calibration solution for said sensor means.

6. An apparatus as claimed in claim 5 wherein said control means comprises means for releasing said calibration solution to said sensor means for calibrating said sensor means.

7. An apparatus as claimed in claim 1 wherein said sensor means comprises a plurality of sensor elements respectively contained in said plurality of disposable cassettes, a single analyzing unit, and a plurality of interface means respectively contained in said plurality of disposable cassettes for providing a communication interface between the sensor element in a cassette and said control means while fluid is flowing in that cassette.

8. An apparatus as claimed in claim 1 further comprising a measurement station at which said sensor means are disposed, wherein said transfer means comprises means for successively bringing said cassettes individually into and out of connection with said measurement station, and wherein said control means comprises means for controlling said transfer means for bringing each cassette into connection with said measurement station after that cassette has been filled with an amount of said fluid from said fluid sampling means.

9. An apparatus as claimed in claim 8 wherein said transfer means comprises a tube and means for transporting a cassette through said tube from said cassette magazine into fluid communication with said fluid sampling means.

10. An apparatus as claimed in claim 9 wherein said transfer system comprises means for pneumatically transporting said cassette through said tube.

11. An apparatus as claimed in claim 9 wherein said transfer system comprises means for mechanically transporting said cassette through said tube.

12. An apparatus as claimed in claim 9 wherein said transfer system comprises means for electromagnetically transporting said cassette through said tube.

13. An apparatus as claimed in claim 1 wherein each disposable cassette comprises a filling detector for sensing an amount of fluid entered into said cassette.

14. An apparatus as claimed in claim 1 wherein said fluid sampling means comprises means for drawing blood from said subject and wherein said sensor means comprises means for analyzing a blood gas content of blood in a cassette in fluid communication with said fluid sampling means.

15. An apparatus as claimed in claim 1 wherein said sensor means comprises an optical sensor element.

16. An apparatus as claimed in claim 1 wherein said sensor means comprises an electrochemical sensor element.

17. An apparatus as claimed in claim 1 wherein said sensor means comprises an optical sensor element and an electrochemical sensor element.

18. An apparatus as claimed in claim 1 wherein said fluid sampling means comprises a sample membrane adapted for connection to said fluid.

19. An apparatus as claimed in claim 1 wherein each cassette comprises a cassette membrane separating an interior of said cassette from an exterior of said cassette.

20. An apparatus as claimed in claim 19 further comprising an interior evacuated volume in said cassette.

21. An apparatus for analyzing body fluids from a living subject comprising: fluid sampling means continuously in fluid communication with to a living subject for drawing a fluid therefrom for the duration of a fluid sampling procedure;

a cassette in fluid communication with said fluid sampling means through which fluid drawn from said subject flows;

a sensor magazine containing a plurality of disposable sensor elements;

transfer means for successively bringing sensor elements individually from said sensor magazine into and out of communication with said fluid in said cassette for analyzing said fluid in said cassette; and control means for controlling said transfer means to successively bring said sensor elements individually into and out of communication with said fluid in said cassette at a programmable rate.

* * * * *